United States Patent
Burke et al.

(10) Patent No.: US 6,673,370 B2
(45) Date of Patent: Jan. 6, 2004

(54) OXIDIZED COLLAGEN FORMULATIONS FOR USE WITH NON-COMPATIBLE PHARMACEUTICAL AGENTS

(75) Inventors: David J. Burke, Oakland, CA (US); Son I. Kuan, San Jose, CA (US)

(73) Assignee: BioMedicines, Inc., Emeryville, CA (US)

( * ) Notice: Subject to any disclaimer, the term of this patent is extended or adjusted under 35 U.S.C. 154(b) by 119 days.

(21) Appl. No.: 09/858,247

(22) Filed: May 15, 2001

(65) Prior Publication Data

US 2002/0187191 A1 Dec. 12, 2002

(51) Int. Cl.$^7$ ................................................. A61K 9/14
(52) U.S. Cl. ....................................................... 424/484
(58) Field of Search .......................... 424/484; 530/350, 530/356

(56) References Cited

U.S. PATENT DOCUMENTS

| | | |
|---|---|---|
| 4,619,913 A | 10/1986 | Luck et al. |
| 5,013,553 A | 5/1991 | Southard et al. |
| 5,750,146 A | 5/1998 | Jones et al. |

OTHER PUBLICATIONS

Bacakova, L., et al. "Oxidized Collagen Stimulates Proliferation of Vascular Smooth Muscle Cells." *Experimental and Molecular Pathology.* 64: 185–194 (1997) Article No. MO972219, Academic Press.

Komsa–Penkova, R., et al. "Discrete reduction of type I collagen thermal stability upon oxidation." *Biophysical Chemistry.* 83: 185–195 (1999) Elsevier Science B.V.

Lippman, R.D., et al. "Rapid In Vivo Quantification and Comparison of Hydroperoxides and Oxidized Collagen in Aging Mice, Rabbits and Man." *Experimental Gerontology.* 20: 1–5 (1985) Pergamon Press Ltd.

Wells–Knecht, M.C., et al. "Age–dependent Increase in Ortho–Tyrosine and Methionine Sulfoxide in Human Skin Collagen is Not Accelerated in Diabetes." *J. Clin. Invest.* 100(4): 839–846 (1997) American Society for Clinical Investigation, Inc.

*Primary Examiner*—Karen Cochrane Carlson
*Assistant Examiner*—Sheridan K Snedden

(57) ABSTRACT

Disclosed are oxidized collagen compositions wherein the thiomethyl group of one or more of the methionine residues of the collagen have been replaced with methylsulfoxy and/or methylsulfonyl groups.

11 Claims, 2 Drawing Sheets

Fibrillogenesis Profile of Oxidized Collagen Solutions

Fibrillogenesis Profile of Oxidized Collagen Solutions

| Sample | Final O.D.(313 nm) | $t_{1/2}$ (minutes) |
|---|---|---|
| Control | 1.2962 | 24.4 |
| 2/98 batch | 1.0432 | 35.1 |
| 3/98 batch | 0.9649 | 41.0 |

US 6,673,370 B2

OXIDIZED COLLAGEN FORMULATIONS FOR USE WITH NON-COMPATIBLE PHARMACEUTICAL AGENTS

BACKGROUND OF THE INVENTION

FIELD OF THE INVENTION

This invention is directed to novel collagen compositions and to methods of using such compositions. In particular, the collagen compositions of this invention are directed to oxidized collagen compositions wherein the thiomethyl group of one or more of the methionine residues of the collagen has been replaced with methylsulfoxy and/or methylsulfonyl groups.

Surprisingly, the oxidized collagen compositions described herein are compatible with pharmaceutical drugs which are otherwise non-compatible with non-oxidized collagen. Accordingly, the oxidized collagen compositions described herein provide for improved drug delivery, administration, clinical utility and/or therapeutic use of certain non-compatible pharmaceutical drugs, particularly cytotoxic drugs, when used in combination with the oxidized collagen. In addition, the oxidized collagen compositions described herein will provide for improved drug delivery when used with compatible pharmaceutical drugs.

REFERENCES

The following publications are cited in this application as superscript numbers:

[1] Southard, et al., Drug Delivery Devices, U.S. Pat. No. 5,013,553 issued on May 7, 1991
[2] Luck, et al., Treatments Employing Drug-Containing Matrices for Introduction into Cellular Lesion Areas, U.S. Pat. No. 4,619,913, issued Oct. 28, 1986
[3] Jones, et al., Translucent Collagen Formulations with a Cytotoxic Drug, U.S. Pat. No. 5,750,146, issued May 12, 1998

All of the above references are herein incorporated by reference in their entirety to the same extent as if each individual reference was specifically and individually indicated to be incorporated herein by reference in its entirety.

STATE OF THE ART

Collagen is a well known biomaterial having many uses in medicine, including, for example, use as a hemostat, use in soft tissue augmentation, use for treatment of urinary incontinence, and use as a drug delivery platform. Examples of use of collagen as a drug delivery platform include collagen compositions comprising a benzo(c)phenanthridine alkaloid or a cytotoxic drug.[1,2]

Collagen can be formulated with, for example, cytotoxic drugs, where the collagen is used as a drug delivery device to locally administer the drug to a patient while minimizing systemic uptake.[2,3] In certain instances, the drug is compatible with the collagen for only a limited period of time and subsequently becomes non-compatible with the collagen, thereby inhibiting the effectiveness of the preparation and often adversely affecting its administration to the patient. Without being limited to any theory, it is believed that this non-compatiblity arises by undesirable reactions, such as cross-linking, between the non-compatible drug and the collagen chains. Cisplatin, for example, has a tendency to react with protein, nucleic acid, and other substances with nucleophilic groups. When cisplatin is combined into an aqueous collagen gel, the resulting preparation becomes progressively, over time, more rigid and inhomogeneous, and cisplatin recovery is decreased. It is further believed that the cisplatin reacts with nucleophilic groups in the collagen resulting in collagen cross-linking.

In affecting the ability to form physically and chemically stable collagen-based formulations, such reactions both impair the therapeutic activity of the non-compatible pharmaceutical drug and change the rheologic characteristics of the preparation, making the material variable in efficacy and difficult to administer.

Because of this non-compatibility, it is necessary to mix cisplatin with the collagen composition just prior to administration, and to complete the administration within several hours after mixing.

In one embodiment, this invention is directed to the discovery that oxidation of the thiomethyl group in one or more methionine residues in collagen to the corresponding methylsulfoxy or methylsulfonyl group renders the resulting collagen composition more compatible with otherwise non-compatible drugs. In this regard, collagen generally exists as long, rod-shaped molecules that are comprised of a triple helix formed as either a homo- or heterotrimer from three polypeptide chains. The primary structure is characterized by glycine-X-Y repeats, where a significant number of the X's are proline or hydroxyproline and Y comprises other amino acid residues, including methionine and histidine residues. At physiological pH, the individual collagen molecules self-assemble into microscopic or macroscopic fibrils or networks, which provide the typical extracellular matrix scaffolding exhibited by collagen. When collagen is used in drug delivery applications, fibrillar collagen can act as a thickening agent in aqueous systems, providing a viscous gel-like material. Collagen can also be dried into pellet-like forms for use in sustained-release implants.

Many pharmaceutical drugs are believed to be non-compatible for use with collagen formulations because they contain functional groups that, over time, can participate in undesirable reactions with collagen, e.g., they can react with the methionine residues of collagen. These undesirable reactions can result in cross-linking between the non-compatible drug and the collagen chains. As noted above, such cross-linking significantly impairs the effectiveness of the collagen/pharmaceutical drug composition.

SUMMARY OF THE INVENTION

This invention relates to oxidized collagen compositions wherein the thiomethyl group of one or more of the methionine residues of the collagen is replaced by methylsulfoxy and/or methylsulfonyl groups. As noted above, such compositions have improved compatibility with cytotoxic drugs such as cisplatin which drugs are otherwise non-compatible upon prolonged contact with the collagen.

Accordingly, in one of its composition aspects, this invention is directed to oxidized collagen wherein the thiomethyl group of one or more of the methionine residues of the collagen have been replaced by methylsulfoxy and/or methylsulfonyl groups.

Preferably, at least 20% of the methionine residues of the collagen have been replaced by methylsulfoxy and/or methylsulfonyl groups. More preferably, at least 40% and still more preferably at least 60% of the methionine residues of the collagen have been replaced by methylsulfoxy and/or methylsulfonyl groups.

This invention is also directed to the discovery that replacement of one or more of the methionine residues in collagen with methylsulfoxy and/or methylsulfonyl groups prior to addition of a non-compatible pharmaceutical drug reduces or prevents undesirable reactions, such as cross-linking, between the non-compatible drug and collagen thereby rendering the non-compatible drug more compatible with collagen. Without being limited to any theory, it is believed that replacement of methionine thiomethyl groups by methylsulfoxy and/or methylsulfonyl groups reduces or prevents reactions between the sulfur nucleophile in the methionine and non-compatible drugs. Also surprisingly and unexpectedly, this replacement does not substantially affect the ability of the collagen molecules to form fibrils and, accordingly, does not affect the properties of the collagen to act as a carrier for the pharmaceutical drug.

In addition, such a reduction in undesirable reactions also permits formulations comprising compatible drugs which, in some cases, may provide for one or more improved features such as improved shelf-life, improved efficacy, and the like.

Accordingly, in another of its composition aspects, this invention is directed to a pharmaceutical composition comprising:
  a) oxidized collagen wherein the thiomethyl group of one or more of the methionine residues of the collagen have been replaced by methylsulfoxy and/or methylsulfonyl groups; and
  b) a pharmaceutical drug.

The pharmaceutical drug employed in these compositions can either be compatible or non-compatible with non-oxidized collagen. However, the benefits of oxidized collagen are most pronounced when the drug is otherwise non-compatible with non-oxidized collagen. Preferably, the pharmaceutical drug is a cytotoxic drug and more preferably is a platinate.

This invention is also directed to the discovery that undesirable reactions between collagen and non-compatible pharmaceutical drugs are reduced when the formulation is acidified, i.e, when the pH of the formulation is lowered to less than about 4.5 (e.g., to pH 3.7) and more preferably from about 2.5 to 4.5. It is believed that acidification of the collagen formulation protonates histidine residues in collagen reversing, reducing or preventing reactions between histidine residues and non-compatible drugs. It has been found that the benefits of acidification can be achieved either by acidification of the collagen formulation prior to or after the addition of a non-compatible drug.

It has been still further found that undesirable reactions between collagen and non-compatible pharmaceutical drugs are reduced when the concentration of collagen used in the formulation is reduced. Preferably, the amount of collagen in the formulation is about 3% w/w or lower and more preferably from about 1% w/w to about 3% w/w.

The benefits of acidification of the collagen composition in combination with the pharmaceutical drug is achieved either alone or in combination with use of oxidized collagen. Accordingly, in another of its composition aspects, this invention is directed to a pharmaceutical composition comprising collagen and a pharmaceutical drug wherein the pH of said composition is less than about 4.5. Preferably, the pH of the composition is from about 2.5 to about 4.5 and more preferably is about 3.7.

In another preferred embodiment, the collagen employed in the acidified collagen composition is oxidized collagen as described herein.

In one of its method aspects, this invention is directed to a method for rendering non-compatible drugs compatible with collagen which method comprises replacing one or more of the collagen's methionine thiomethyl groups with methylsulfoxy and/or methylsulfonyl groups. In one embodiment, this replacement may be achieved by contacting a collagen composition with an oxidizing agent under conditions wherein one or more of the collagen's methionine thiomethyl groups are converted to methylsulfoxy and/or methylsulfonyl groups. Suitable oxidizing agents are well known in the art and preferably include hydrogen peroxide, meta-chloro perbenzoic acid, and the like.

Alternatively, oxidized collagen wherein one or more of the collagen's methionine thiomethyl groups are replaced with methylsulfoxy and/or methylsulfonyl groups can be prepared by routine protein chemistry. For example, standard solid phase synthesis can be used to insert an oxidized methionine residue in place of the methionine residue into the growing peptide.

The method described above may further include lowering the pH of the collagen composition to less than or equal to 3.7; and/or lowering the concentration of the collagen in the formulation to about 3% w/w or lower.

In another of its method aspects, this invention is directed to a method for treating neoplastic lesions or surrounding tissue which method comprises introducing at the site of the lesion or tissue surrounding the lesion a pharmaceutical composition comprising:
  (a) a collagen composition selected from the group consisting of oxidized collagen, collagen acidified to a pH of from about 2.5 to about 4.5, and oxidized collagen acidified to a pH of from about 2.5 to about 4.5; and
  (b) a pharmaceutically acceptable cytotoxic drug.

DETAILED DESCRIPTION OF THE PREFERRED EMBODIMENTS

Figure 1:
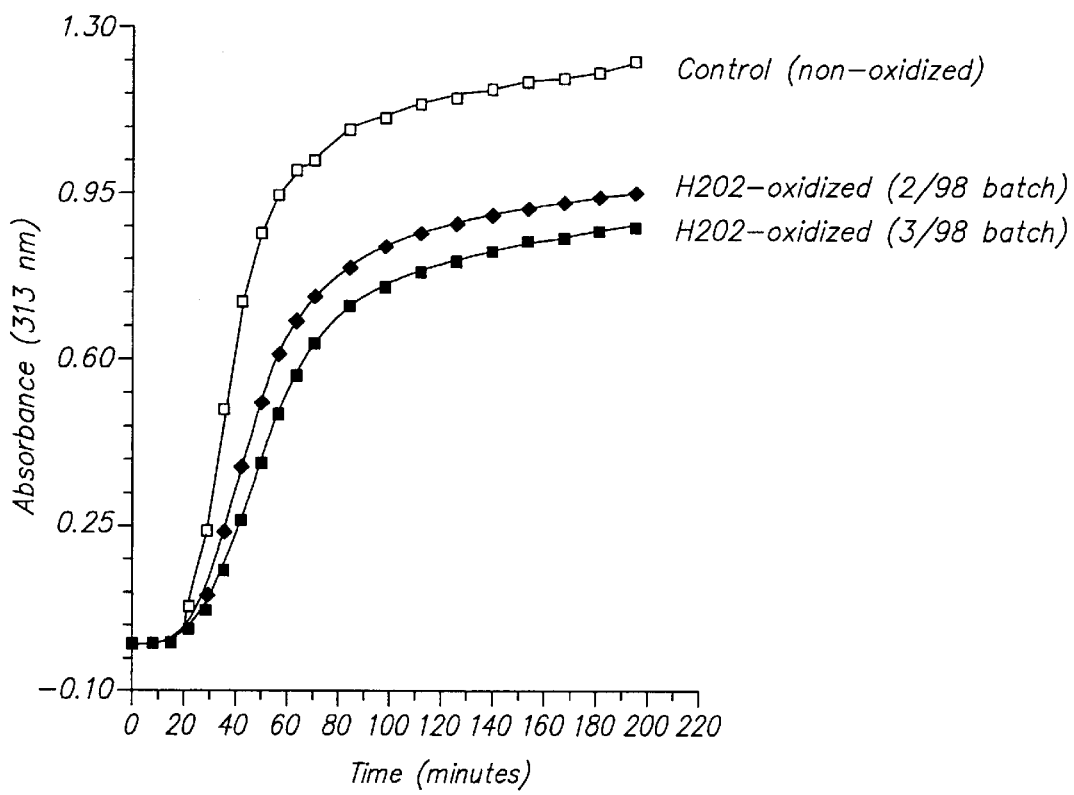
FIG. 1 illustrates a Fibrillogenesis Profile of Oxidized Collagen Solutions.

This invention is directed to novel collagen formulations adapted for use with pharmaceutical drugs (particularly non-compatible pharmaceutical drugs) and methods for using such novel collagen formulations.

When used with non-compatible pharmaceutical drugs, the collagen formulations and methods described herein provide for improved drug delivery, administration, clinical utility and/or therapeutic effect of non-compatible pharmaceutical drugs, particularly cytotoxic drugs. In addition, the collagen compositions described herein can be used with compatible pharmaceutical agents. Prior to describing this invention in further detail, the following terms will first be defined:

The phrases "non-compatible pharmaceutical drug" or "non-compatible drug" refer to one or more pharmaceutical drugs which, over time, participate in undesirable reactions, such as cross-linking, with un-modified collagen. Accordingly, these terms include drugs which, while initially compatible with unmodified collagen for a limited period of time, become non-compatible over time with the unmodified collagen.

These undesirable reactions impair the drug delivery, administration, clinical utility and/or therapeutic use of the non-compatible drug particularly those which have been stored for prolonged periods of time (e.g., greater than 24 hours). Crosslinking of the non-compatible drug with the collagen can be quantified by measuring the force required to extrude a collagen gel through a needle at a fixed delivery rate. The greater the degree of crosslinking, the more difficult the collagen formulation will be to extrude. Examples of non-compatible pharmaceutical drugs include the well known platinate family of drugs including cisplatin.

The phrases "compatible pharmaceutical drug" or "compatible drug" refer to one or more pharmaceutical drugs whose reactions with unmodified collagen do not significantly impair the use of a collagen formulation comprising such a drug in combination with the unmodified collagen. Examples of compatible pharmaceutical drugs include fluorouracil, methotrexate and the like.

The phrase "platinates" refers to cytotoxic drugs that contain platinum as a central atom. Examples of platinates include cisplatin, carboplatin, oxaliplatin, ormaplatin, iproplatin, enloplatin, nedaplatin, ZD0473 (cis-amminedichloro(2-methylpyridine)-platinum (II)), BBR3464 and the like.

The phrase "oxidized collagen" refers to collagen comprising at least one methionine residue therein wherein the thiomethyl group of one or more of the methionine residues of the collagen has been replaced by methylsulfoxy and/or methylsulfonyl groups. This replacement can occur by, for example, contacting a collagen composition with an oxidizing agent under conditions wherein one or more of the collagen's methionine thiomethyl groups are converted to methylsulfoxy and/or methylsulfonyl groups. Alternatively, this replacement can occur wherein one or more of the collagen's methionine thiomethyl groups are replaced with methylsulfoxy and/or methylsulfonyl groups by routine protein chemistry.

Preferably, at least 20% of the thiomethyl groups of the methionine residues of the collagen have been replaced by methylsulfoxy and/or methylsulfonyl groups. More preferably, at least 40% and still more preferably at least 60% of the thiomethyl groups of the methionine residues of the collagen have been replaced by methylsulfoxy and/or methylsulfonyl groups.

The term "oxidation" refers to any method of oxidation of the collagen formulation, including treatment of the collagen with hydrogen peroxide.

The term "acidification" refers to any method of lowering the pH of the collagen formulation either before or after combination with a non-compatible pharmaceutical drug. Preferably, acidification employs a pharmaceutically acceptable acid to lower pH. Suitable pharmaceutically acceptable acids are well known in the art and include, by way of example only, hydrochloric acid, phosphoric acid, acetic acid, citric acid, lactic acid, and the like.

The term "transition temperature" means the temperature where the collagen in the aqueous collagen composition undergoes a phase change. The phase change is typically a change in the fibril size of the collagen in the composition and can be readily determined by a peak in a conventional Differential Scanning Calorimetry (DSC) scan of the aqueous collagen composition. For purposes of this application, transition temperatures measured by DSC are determined under the following conditions: heating at 10° C. per minute using a DSC instrument available from TA Industries, New Castle, Del., USA.

In one aspect of the present invention, the collagen formulations are adapted for use with non-compatible pharmaceutical drugs by oxidation. Without being limited to any theory, it is believed that oxidation of the collagen replaces at least a portion of the thiomethyl groups of the collagen's methionine residues with methylsulfoxy and/or methylsulfonyl groups thereby reducing or preventing reactions between the nucleophilic sulfur of the un-oxidized thiomethyl group with non-compatible pharmaceutical drugs. In addition, the oxidized collagen formulations of the present invention can be used with compatible pharmaceutical drugs.

To achieve the benefits of the invention, it is not critical that all of the thiomethyl groups are replaced by methylsulfoxy and/or methylsulfonyl groups. Replacement of any portion of the thiomethyl groups reduces the number of undesired interactions between collagen and the non-compatible drug. Preferably, at least 20% of the thiomethyl groups of the methionine residues of the collagen have been replaced by methylsulfoxy and/or methylsulfonyl groups. More preferably, at least 40% and still more preferably at least 60% of the thiomethyl groups of the methionine residues of the collagen have been replaced by methylsulfoxy and/or methylsulfonyl groups.

In order to avoid impairing the therapeutic effect of the pharmaceutical drug, it is important that oxidation of the collagen occurs prior to the addition of the drug.

In another aspect of the present invention, the collagen formulation is acidified, i.e., the pH of the collagen formulation is lowered. Without being limited to any theory, it is believed that acidification of the collagen formulation protonates histidine residues reversing, reducing or preventing undesirable reactions between the histidine residues and non-compatible drugs.

To achieve the benefits of the invention, it is not critical that all of the histidine residues in the collagen are protonated. Any lowering of the pH of the collagen formulation below the neutral pH of 7 decreases the undesired interactions between the collagen and the non-compatible drug. However, in a preferred embodiment of the invention, the pH of the collagen composition is lowered to between 2.5 and 4.5, and more preferably is about pH 3.7.

Compositions

In one embodiment, the compositions described herein comprise oxidized collagen, a pharmaceutical drug and a physiologically acceptable aqueous medium in which the collagen is dispersed. The drug may be dissolved, dispersed or complexed with the collagen.

The oxidized collagen employed in the compositions described herein is derived from collagen which, in turn, can be derived from any mammalian host source, such as bovine, porcine or human and can also be produced by recombinant DNA or transgenic production techniques. The collagen employed may be natural collagen or may be modified, such as tropocollagen, atelocollagen, or the like. The collagen may be non-immunogenic, immunogenic, or only slightly immunogenic.

Various methods of preparing collagen or derivatives thereof in purified form for administration to a mammalian host are known in the art. Suitable methods include those recited in, for example, U.S. Pat. No. 3,949,073 and references cited therein. Of interest is bovine collagen which is purified and is obtained from young cattle. Isolation and purification will normally involve dispersion or precipitation from various media, e.g., dilute acetic acid. In some situations, xenogeneic collagen is employed to enhance an immunogenic response in the area of injection or immunogenic adjuvants may be employed. Additionally, collagen suitable for use herein is also commercially available from a number of vendors.

As noted above, in this embodiment, collagen is oxidized prior to addition of the pharmaceutical drug. In one embodiment, oxidation of collagen is accomplished by contacting collagen, typically in an aqueous solution, with an oxidizing agent such as hydrogen peroxide. The degree of oxidation is controlled by the amount of oxidizing agent employed, the contact time and the contact temperature. Preferably, an excess (typically from about 2 to about 50 stoichiometric equivalents) of oxidizing agent is employed based on the total number of methionine residues in the collagen. The oxidation reaction is likewise preferably conducted for a period of from about 0.1 to about 100 hours, and more preferably from about 1 to about 10 hours, at a temperature of from about 0° to about 40° C. At the completion of the reaction, oxidized collagen is recovered by conventional means.

The specific concentration of oxidizing agent and reaction conditions are selected in order that at least about 20% of the methionine residues in the collagen are replaced by methylsulfoxy and/or methylsulfonyl groups. More preferably, at least about 40% and still more preferably at least about 60% of the methionine residues of the collagen have been replaced by methylsulfoxy and/or methylsulfonyl groups. The specific selection of concentration and reaction conditions based on these parameters are well within the skill of the art.

In one embodiment, sufficient amounts of the oxidized collagen are employed in the aqueous composition to provide for an oxidized collagen concentration of from about 5 to about 100 mg/mL and preferably from about 5 to about 75 mg/mL. The specific amount of oxidized collagen employed is selected relative to the desired viscosity of the oxidized collagen composition such that the composition will flow under moderate pressure, but not move significantly after being positioned at a particular site in the patient. Preferably, sufficient oxidized collagen is employed such that the composition will have a viscosity of from about 5,000 to about 20,000 centipoise at 20° C. and at a shear rate of 15.8 sec$^{-1}$.

In another embodiment, the amount of oxidized collagen in the formulation is lowered to about 3% w/w or lower and more preferably, to from about 1% w/w to about 3% w/w.

In another embodiment, an acidified aqueous collagen composition is employed in combination with the pharmaceutical drug. In this embodiment, the acidified collagen composition employs a pharmaceutical drug and either collagen, oxidized collagen or a mixture thereof at the concentrations recited above. In addition, a sufficient amount of a pharmaceutically acceptable acid is added to the composition to adjust the pH to about 2.5 to 4.5. The addition of the pharmaceutically acceptable acid is typically conducted at room temperature and the concentration of the collagen and/or oxidized collagen employed in the composition is adjusted so that the desired concentration is achieved upon addition of the acid.

Whether using oxidized collagen, acidified collagen, or acidified and oxidized collagen, the pharmaceutical drug is used individually or in combination, depending upon the nature of the drug, the therapeutic use of the drug, and whether cooperative action is pharmaceutically indicated. Preferably, the drug is a non-compatible pharmaceutical drug such as a platinum-based drug, e.g., cisplatin (cis-diamminedichloroplatinum (II)). In a particularly preferred embodiment, the cisplatin is employed at a concentration of greater than about 0.1 mg/mL and still more preferably from greater than about 1.0 mg/mL to about 10.0 mg/mL in the composition.

The pharmaceutical drug may be unbound to the collagen or bound through non-covalent binding such as complexation, salt formation, coordination complexes, or the like, but any binding should be readily reversible and should not result in significant diminution of the physiological activity of the drug. The pharmaceutical drug may also be modified by, for example, introduction of bonds which allow for enzymatic cleavage, e.g., hydrolysis, of the drug from a carrier other than collagen.

These modifications will depend upon the individual pharmaceutical drug, varying the solubility of the drug in the aqueous medium and providing for non-covalent interactions with the collagen. In addition, various physiologically acceptable bulking drugs or concentrating drugs may be optionally employed which serve to provide for drug and protein interactions, with resulting reduction in the rate of drug release. Illustrative materials include inorganic substances, such as hydroxyapatite and organic substances such as carbohydrates, e.g., dextran, agarose, methyl cellulose and cellulose.

The compositions of this invention may still further include other drugs in combination with the pharmaceutical drugs so as to reduce physiological insult and/or to restrict regional vasculature, either as to growth and/or passage opening, e.g., vasoconstrictive or sympathomimetic drugs. These drugs may include catecholamines, e.g., epinephrine and norepinephrine, dipivefrin, epinephryl borate, ergot alkaloids, prostaglandins, angiotensin or the like. Other agents for affecting tissue architecture include enzymes which can injure the stroma, such as the peptidases papain, chymopapain, trypsin, amylase, collagenase and chymotrypsin. Or drugs affecting cellular permeability may be employed, such as non-ionic detergents, e.g., polysorbate, amphotericin B, dimethylsulfoxide, and anaesthetics such as procaine. In a particularly preferred embodiment, epinephrine is employed in conjunction with the collagen composition.

Besides xenogeneic collagen, other materials may be included to enhance an immunogenic response, e.g., proliferation and invasion of macrophage, helper T-cells, etc. Illustrative adjuvants include *Corynebacterium parvum*, Bacillus Calmette-Guerin cell wall or cell wall skeleton preparations, *Mycobacterim bovis* and the like. See for example, Miyata et al., *Cancer Res.*, 43:4670–4675 (1983); Bier et al., *Arch. Otorhinolaryngol*, 236:245–255 (1982); and Mehanjhlin et al., *Cancer Res.*, 38:1311–1316 (1978) which references are incorporated by reference in their entirety.

For enhancing cytotoxic activity various adjuvant materials may be incorporated into the collagen, such as radioactive pellets, e.g., radionucleides technetium or iridium; radiation sensitizers, e.g., misonidazole; repair inhibitors, e.g., methylated xanthines; bioreductive drugs, which are activated only in hypoxic cells; immunomodifiers, such as interferons, lymphokines, such as interleukin-2, tumor growth inhibitors, such as tumor necrosis factor, transforming growth factor-β, and the like, and/or angiographic contrast media.

In a preferred embodiment, the collagen (including oxidized collagen, acidified collagen or oxidized and acidified collagen), pharmaceutical drug and certain optional additives are uniformly dispersed in a physiologically acceptable aqueous medium, such as saline, phosphate buffered saline, distilled water, etc. to form a collagen composition. The aqueous medium will be sufficient to provide for an amorphous dispersion capable of flowing under mild pressure. Usually, the liquid aqueous medium will be at least 90 weight percent of the entire composition, more usually at least 95% weight percent, usually not more than about 99.5 weight percent, so as to provide a flowable mixture. The amount will vary depending upon the nature of the pharmaceutical drug, the presence of other materials and the like.

Optional additives can also be included in the composition for a variety of purposes. These additives will for the most part impart properties which protect the stability of the composition, control the pH, or the like. Illustrative agents include phosphate and acetate buffers, methyl or propyl paraben, polyethylene glycols, and the like. These agents will generally be present in less than about 2 weight percent of the total composition, usually less than about 1 weight percent, and individually may vary from 0 to about 1 weight percent.

The compositions described herein can be prepared by combining the collagen, the pharmaceutical drug and the physiologically acceptable aqueous medium in a sterile environment. Optional additives may also be included at this time although certain additives such as vasoconstrictive or sympathomimetic drugs, due to stability problems, may preferably be incorporated into the composition just prior to use. The collagen will be provided in a convenient form, usually admixed with at least a portion of the total aqueous medium to be employed. The composition will be sufficiently workable that upon admixture, a uniform dispersion can be obtained. The pharmaceutical drug may be added to the collageneous dispersion with agitation to ensure the uniform dispersion of the drug. Optional materials, as appropriate, may be added concomitantly or sequentially. Sterility will usually be maintained using aseptic conditions.

The subject compositions are useful in the chemotherapeutic (cytotoxic) treatment of a wide variety of neoplastic lesions involving solid abnormal tumors, cellular growth, or adjacent tissues which may contain abnormal tumor cells. The composition is injected into the lesion, e.g., tumor or lesion area (tissue adjacent to the lesion), or in those situations where the tumor has been removed, tissue adjacent to the previously removed tumor. The composition is flowable for injection, but provides for stable placement, once injected into the tissue. That is, once injected the collagen resists mechanical disruption and does not migrate significantly. After injection, the cytotoxic drug is released into the immediate environment, so as to prevent substantial transportation of the drug to other sites, where its cytotoxic activity is undesirable.

Illustrative tumors include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectals cancer, brain tumors, mycosis fungoides, Hodgkin's lymphoma, polycythemia vera, chronic granulocytic leukemia, lymphomas, oat cell sarcoma, and the like. Tumors may also include benign growths such as condylomata acuminata (genital warts) and moles and common warts.

The subject composition will be administered to a tumor to provide a cytotoxic amount of a cytotoxic drug at the tumor site. The amount of cytotoxic drug administered to the tumor site will preferably range from about 0.01 to 100 mg/kg of host, more usually about 0.5 to 300 mg/kg of host, depending upon the nature of the drug, size of the tumor, and other considerations. When employed, the vasoconstrictive agents will generally be present in from about 1 to about 50 weight percent of the cytotoxic drug. With each drug in each tumor, the specific amount of cytotoxic drug employed will depend on factors such as the type and/or nature of the tumor to be treated, the cytotoxic drug to be used, the relative mobility of the cytotoxic drug, and the like. Such factors are well within the skill of the art.

Unless otherwise stated, all temperatures are in degrees Celsius. Also, in these examples, unless otherwise defined below, the abbreviations employed have their generally accepted meaning:

| | |
|---|---|
| cisplatin, CDDP = | cis-diamminedichloroplatinum (II) |
| CNBr = | cyanogen bromide |
| Da = | Dalton |
| DSC = | differential scanning calorimetry |
| g = | gram |
| G = | gauge |
| HPLC/SEC = | size exclusion high performance liquid chromatography |
| M = | Molar |
| mg = | milligrams |
| mL = | milliliters |
| mm = | millimeter |
| N = | Newton |
| OD = | optical density |
| Pa = | Pascal |
| RT = | room temperature |
| SDS-PAGE = | sodium dodecyl sulfate mediated polyacrylamide gel electrophoresis |
| sec = | second |
| % w/w = | percent weight to weight |

EXAMPLES

In the following examples, Example 1 illustrates the preparation and characterization of oxidized collagen.

Example 2 illustrates the reduced reactivity of cisplatin with oxidized collagen compared to non-oxidized collagen.

Example 3 illustrates further improvement in CDDP/collagen mixed gel stability after formulation at a low pH in a gel with reduced collagen content.

Example 1

Preparation of Oxidized Collagen

A. Preparation of Oxidized Collagen

Type I bovine collagen (containing a small amount of Type III collagen) was obtained from a ground suspension of young bovine hides by acid treatment, pepsin digestion, removal of solids, and ultrafiltration/diafiltration. This resulted in a 0.6% (w/v) collagen solution in 10 mM HCl.

Methionine residues in this collagen solution were oxidized by slowly adding 0.86 mL of 30% hydrogen peroxide to 800 mL of the collagen solution and mixing. This combination resulted in a 25-fold molar excess of peroxide to total methionine residues in the collagen. The mixture was stirred at room temperature for one hour and then stored at 2–8° C. for approximately 60 hours.

Collagen fibers were then precipitated by adding one volume of 0.2M sodium phosphate buffer, pH 10.7, to 9 volumes of the oxidized collagen solution (the final pH was approximately 7.2).

After stirring for 2 hours, the precipitate was collected by centrifugation. The collagen pellet was washed twice with approximately 600 mL of 20 mM sodium phosphate/9 mM NaCl (pH 7.2) to remove residual hydrogen peroxide. The washed oxidized-collagen concentrate (approximately 85 mg collagen per gram of slurry) was then further formulated by addition of water and 0.6 M sodium phosphate/0.27 M NaCl buffer (pH 6.8) to yield a homogeneous gel with a target composition of 65 mg/g oxidized-collagen (6.5% collagen gel), 0.1 M sodium phosphate and 0.045 M NaCl.

A non-oxidized collagen gel with the same final composition was produced from the same lot of 0.6% collagen solution by leaving out the hydrogen peroxide step.

B. Comparison of CNBr Cleavage of Oxidized and Non-Oxidized Collagen

The extent of oxidation in the oxidized collagen formulation was characterized by a cyanogen bromide cleavage assay. Cyanogen bromide cleaves the polypeptide chain at methionine residues, but does not cleave at methionine residues in which the thiomethyl group has been oxidized to methylsulfoxy or methylsulfonyl.

Oxidized and non-oxidized collagen samples of both the 0.6% collagen solutions and the 6.5% collagen gels were subjected to cyanogen bromide cleavage, and the resulting fragments were separated by SDS-PAGE (10–20% tris glycine gel) and stained with Coomassie Blue to look for differences in the fragmentation patterns. Non-oxidized collagen solution and gel both showed numerous bands in the 25–80 kDa molecular weight range and no bands above about 90 kDa, demonstrating efficient cleavage by CNBr. The CNBr digests of oxidized collagen solution and gel lacked the lower molecular weight bands found in the non-oxidized controls, and instead showed bands above 100 kDa. These results indicate that peroxide treatment oxidized most of the methionine residues in the collagen.

C. Comparison of Optical Rotation of Oxidized and Non-Oxidized 0.6% Collagen Solutions In order to determine whether oxidized collagen would have similar physical and chemical properties to non-oxidized collagen, Applicants measured the specific optical rotation of each formulation.

Type I and Type III collagens are triple helical structures in which each triple helical monomer contains three protein chains. The highly ordered triple helical structure gives collagen a uniquely high optical activity, and unwinding of the helix results in loss of this optical activity.

As shown in TABLE I, specific optical rotation measurements were taken for oxidized and non-oxidized 0.6% collagen solutions (prepared as described above in Section A). Both the oxidized and the non-oxidized collagen solutions demonstrated similar specific optical rotations, showing that both solutions had a similar triple helix content. This data indicates that the triple helix structure of the collagen is not substantially altered by oxidation.

TABLE I

Physical Properties of Oxidized and Non-Oxidized 0.6% Collagen Solutions

|  | Non-oxidized Collagen | Oxidized Collagen |
| --- | --- | --- |
| Specific optical rotation (°/dm · g/mL) | −358.4 | −360.1 |
| Oligomer content by (HPLC/SEC) | 30% | 36% |

D. Comparison of Oligomer Content of Oxidized and Non-Oxidized 0.6% Collagen Solutions When isolated from bovine skin, pepsinized type I and type III collagen exists as a mixture of collagen monomers and oligomers. The oligomer content of the preparation can have an effect on its fiber-forming properties. In order to determine whether oxidized collagen would have similar physical and chemical properties to non-oxidized collagen, Applicants measured the oligomer content of oxidized and non-oxidized 0.6% collagen formulations (prepared as described above in Section A).

Using size exclusion HPLC, the monomer peak can be separated from the oligomer peak, allowing quantitation of the relative abundances of monomer and oligomer. As shown in TABLE I, the oxidized collagen preparation had a slightly higher oligomer content than the nonoxidized collagen preparation.

E. Comparison of Fibrillogenesis of Oxidized and Non-Oxidized 0.6% Collagen Solution A fibrillogenesis assay was conducted to measure the ability of collagen to form fibrils upon neutralization, in order to determine whether oxidized collagen would have similar physical and chemical properties to non-oxidized collagen. This assay was performed on the oxidized and non-oxidized 0.6% collagen solution prepared as described in Section A.

In this fibrillogenesis assay, 9 volumes of either oxidized or non-oxidized collagen solution (0.5 mg/mL in 10 mM HCl) were placed in a cuvette and were neutralized by addition of one volume of 0.2M sodium phosphate, pH 10.7. As the fibers formed, the solution became more turbid, and this turbidity was monitored using a spectrophotometer at a wavelength of 313 nm. As shown in FIG. 1, the fibrillogenesis profile of the oxidized collagen solution was similar to that of the non-oxidized control.

Figure 2A:
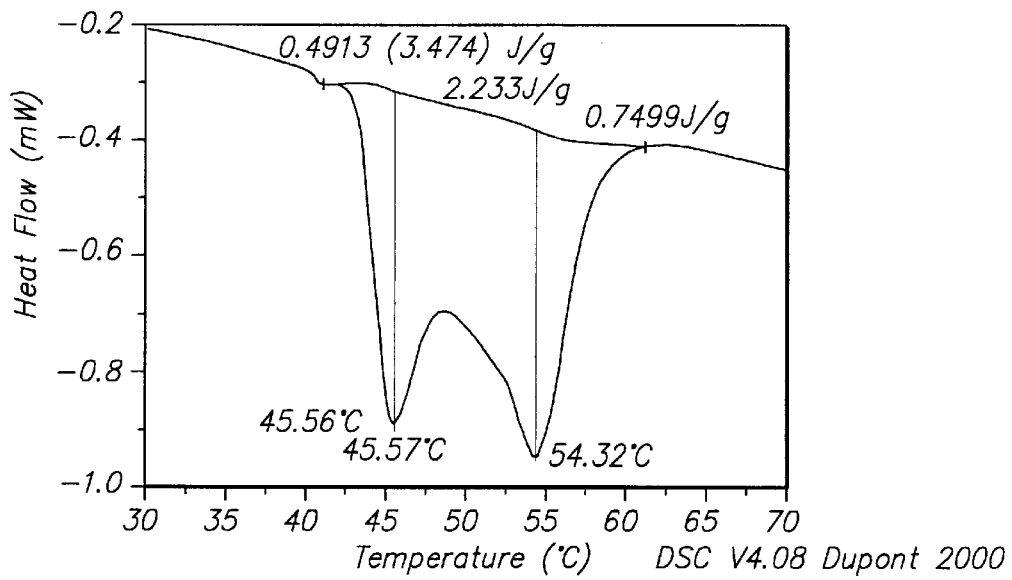
FIGS. 2A–B illustrates a comparison of the DSC Profiles of Non-Oxidized and Oxidized Collagen Gels.
Figure 2B:
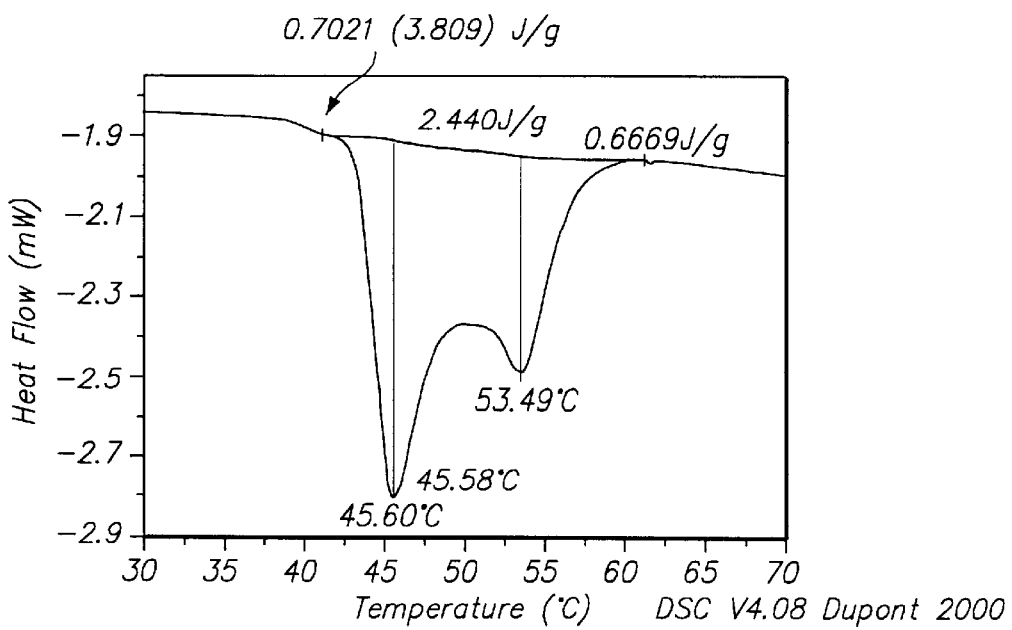

F. Comparison of Physical Properties of Oxidized and Non-Oxidized 6.5% Collagen Gels As described in Section A above, 65 mg/g (6.5%) collagen gels were prepared from oxidized collagen solution and from non-oxidized collagen solution. The physical and biochemical properties of these gels were compared by measuring viscosity, optical rotation, differential scanning calorimetry (DSC) profile, and oligomer content (by HPLC). As shown in TABLE II, the viscosity and specific optical rotation of the oxidized collagen gel were similar to data obtained for the non-oxidized collagen gel. The DSC transition temperatures of both oxidized and non-oxidized collagen were similar at 46° C. and 54° C. As shown in FIGS. 2A–B, the DSC profiles are generally similar. In addition, as shown in TABLE II, the peak height ratios for the two thermal transitions were generally similar. These results suggest that the oxidized collagen gel contained fewer large fibrils and more microfibrils and nonfibrillar collagen than the non-oxidized collagen gel. In this respect, the DSC results were consistent with the fibrillogenesis results presented above.

TABLE II

Physical Properties of Oxidized and Non-Oxidized 6.5% Collagen Gels

|  | Non-Oxidized Collagen | Oxidized Collagen |
| --- | --- | --- |
| Viscosity (mPa · sec @ 15.8/sec) | 16823 | 19013 |
| Specific rotation (°/dm · g/mL) | −345 | −337 |
| DSC transition temperatures | 46° C./54° C. | 46° C./54° C. |
| DSC peak height ratio (46° C./54° C.) | 1.0 | 1.6 |
| Oligomer content (HPLC/SEC) | 43% | 47% |

In summary, reaction of collagen with mild hydrogen peroxide resulted in oxidation of most of the collagen methionyl residues. The resulting oxidized collagen solution was similar in triple helix content, oligomer content, and fiber forming characteristics to the non-oxidized collagen control solution. When this oxidized collagen was precipitated and formulated into a gel, the physical and biochemical properties of this gel were similar to a gel produced from non-oxidized collagen solution.

Example 2

Demonstration of Reduced Reactivity of Cisplatin with Oxidized Collagen

The purpose of this example is to demonstrate the reduced reactivity of cisplatin with collagen gels prepared with oxidized collagen. In this example, oxidized and non-oxidized 6.5% collagen gels were prepared as described in Section A of Example 1, except that the oxidized collagen formulation was obtained by spiking the collagen with methionine sulfoxide, instead of subjecting the collagen to hydrogen peroxide. By spiking the collagen with methionine sulfoxide, many of the methionine residues which would normally be present in the collagen are replaced with oxidized methionine sulfoxide.

The gels were individually mixed with a CDDP suspension, and stored at room temperature for 24 hours. The resulting CDDP/collagen gels (containing 4 mg/ml of CDDP) were analyzed to measure CDDP recovery and extrusion force. The results are reported in TABLE III.

CDDP recovery was measured by a strong anion-exchange HPLC method after dissolution of the CDDP-containing gel in dilute hydrochloric acid.

Extrusion force was measured as the force needed to extrude the gel through a 22 G needle for a prolonged period of time, i.e., several hours. A gel with an extrusion force of less than 15 Newtons (15 N) is easily injected into a tumor through a 22 G needle, while 30 N requires considerable effort and 50 N is not practical.

The CDDP/oxidized-collagen gel demonstrated a higher recovery of CDDP (100%) than the non-oxidized collagen gel (94%). In addition, also as shown in TABLE III, the CDDP/oxidized-collagen gel remained easily extrudible (through a 22 G needle) for a prolonged period of time relative to the corresponding CDDP/non-oxidized collagen gel.

TABLE III

Effects of Collagen Oxidation on Syringeability of CDDP Gels

| Collagen | CDDP Content | Extrusion Force (Newtons) ± SD 5.5 hr | 24 hr |
|---|---|---|---|
| Non-Oxidized | none | 9.2 ± 0.23 | 11.5 ± 0.29 |
| Oxidized | none | 10.6 ± 0.24 | 11.6 ± 0.24 |
| Non-Oxidized | 4 mg/mL | 36.7 ± 2.70 | >50 |
| Oxidized | 4 mg/mL | 11.5 ± 0.17 | 30.2 ± 0.45 |

Example 3

Further Improvement in CDDP/Collagen Mixed Gel Stability After Formulation at Low pH in a Gel with Reduced Collagen Content The purpose of this example is to demonstrate the reduction in undesirable reactions between collagen formulations and CDDP when the collagen and CDDP are formulated at a low pH in a gel with a reduced collagen content.

As noted above, it is believed that some of the undesirable reactions between non-compatible pharmaceutical drugs and collagen are due to reactions between the non-compatible drug, such as CDDP, and the collagen's histidyl residues. Applicants have found that this reaction is readily reversible under acidic conditions. At pH 6.5 and above, the imidazole nitrogens of histidine are weak nucleophiles which can react with cisplatin. Protonation of the imidazole ring below the pK (pH 6.5) make the imidazole ring much less nucleophilic, thereby diminishing its reactivity with CDDP. In addition, since CDDP loss is dependent on the collagen concentration, further formulation improvement is made by reducing the collagen content of the mixed gel.

A. Preparation and Measurement of Physical Properties of Oxidized and Non-Oxidized 3% Collagen Gels at pH 3.7 and pH 7

Oxidized and non-oxidized collagen concentrates were formulated to produce 6% collagen gels (pH 7) in a method similar to that described above. Aliquots of these gels were then mixed with an equal weight of 100 mM phosphoric acid/45 mM NaCl (pH 1.6) to produce 3% collagen gels at a final pH of 3.7. Separate aliquots were formulated with 100 mM sodium phosphate/45 mM NaCl (pH 7) to produce 3.0% gels at a final pH of 7. The physical properties of these four 3% collagen gels were measured and are summarized in TABLE IV.

The physical appearance of the gels was observed. Both of the pH 3.7 gels were clear and colorless, while the pH 7 gels were white and opaque. Over time, the pH 7, oxidized collagen gel remained uniform in consistency but became slightly less opaque after 4 to 24 hours, while the pH 7, non-oxidized gel became rigid and highly aggregated over the same time interval. Over time, the pH 3.7, oxidized collagen gel remained a uniform, clear gel throughout the 24 hour period, while the pH 3.7, non-oxidized gel became noticeably aggregated after 24 hours.

The viscosity of the gels were measured at 20° C. by cone and plate viscometry on a Brookfield Model DV-III HB digital viscometer. All four gels had similar viscosities.

The syringeability or extrusion force for each gel was assessed by measuring the amount of force required to extrude the gel through a 1" 22 G needle. All four gels were easily extrudible.

The DSC profile for all four gels was also measured. For both pH 3.7 gels, the DSC profile displayed a single endotherm at about 42° C., indicative of a non-fibrillar character. The pH 7 gels displayed two DSC endotherms, one at about 45° C. and one at about 52° C., indicative of a more fibrillar structure.

In summary, the oxidized and non-oxidized gels were very similar in each of the measured physical characteristics at each pH.

TABLE IV

Physical Properties of Oxidized and Non-Oxidized 3% (w/w) Collagen Gels Formulated at pH 3.7 or pH 7.0

| Characteristic | Non-Oxidized gel, pH 7.0 | Non-Oxidized gel, pH 3.7 | Oxidized Gel pH 7.0 | Oxidized Gel pH 3.7 |
|---|---|---|---|---|
| Physical appearance | white, opaque | clear, colorless | white, opaque | clear, colorless |
| Viscosity (mPa · sec) @ 15.8/sec | 11,149 | 14,533 | 11,348 | 12,543 |
| Syringeability (extrusion force, N) | 9.0 | 11.2 | 9.2 | 10.1 |
| DSC transition temperatures | 45.1°C. 52.5°C. | 42.6°C. | 45.3°C. 52.7°C. | 42.0°C. |
| Measured pH | 7.05 | 3.75 | 7.02 | 3.69 |

B. Preparation and Measurement of Physical Properties of Oxidized and Non-Oxidized 3% Collagen Gels at pH 3.7 and pH 7.0 formulated with CDDP Lyophilized CDDP was dissolved at 1 mg/mL in 10 mM acetate, pH 4. Four grams of each of the 3.0% collagen gel preparations described in Section A above were mixed with 4 mL of the 1 mg/mL CDDP solution to make mixed gels containing 0.5 mg/mL CDDP in 1.5% (w/w) collagen. At various times after mixing, these gels were sampled and assessed for appearance, pH, viscosity and syringeability.

The syringeability or extrusion force of each gel was measured, as shown in TABLE V. At each pH, the oxidized collagen gels remained more syringeable than the corresponding non-oxidized gels. Over time, particularly at the 24 hour measurement, the pH 3.7 gels generally remained more syringeable than the pH 7.0 gels. At the 24 hour mark, the oxidized collagen pH 3.7 gel evidenced the lowest extrusion force.

TABLE V

Syringeabiity of CDDP Gels Formulated with Oxidized and Non-Oxidized Collagen Gels at pH 3.7 and 7.0

| | Syringeability(N) | | | |
|---|---|---|---|---|
| | Non-Oxidized Collagen | | Oxidized Collagen | |
| Time (hr) | pH 7.0 | pH 3.7 | pH 7.0 | pH 3.7 |
| 0 | 6.0 | 8.8 | 7.3 | 8.0 |
| 2 | 11.0 | 9.0 | 7.8 | 7.7 |
| 4 | 13.9 | 9.4 | 7.7 | 7.6 |
| 6 | 19.7 | 10.0 | 7.7 | 7.7 |
| 24 | >50 | 37.1 | 8.9 | 7.9 |

The viscosity of each gel was measured as shown in TABLE VI. The viscosity of the gels were measured at 20° C. by cone and plate viscometry on a Brookfield Model DV-III HB digital viscometer. This data demonstrates that the viscosity of the oxidized collagen gels were more stable over time than the corresponding non-oxidized gels. In particular, the oxidized collagen gel at pH 3.7 was particularly stable over time.

TABLE VI

Viscosity of CDDP Gels Formulated with Oxidized or Non-Oxidized Collagen Gels at pH 3.7 or 7.0

| | Viscosity (mPa · sec) | | | |
|---|---|---|---|---|
| | Non-Oxidized Collagen | | Oxidized Collagen | |
| Time | pH 7.0 | pH 3.7 | pH 7.0 | pH 3.7 |
| 0 | 2504 | 3363 | 2741 | 2691 |
| 2 | 3168 | 3600 | 2653 | 2753 |
| 4 | 1582 | 4597 | 2691 | 2716 |
| 24 | 6926 | 1445 | 3737 | 3077 |

Finally, the stability of CDDP in the CDDP gels formulated with oxidized and non-oxidized collagen gels at pH 3.7 and pH 7.0 was measured over time. CDDP recovery was measured by a strong anion-exchange HPLC method after dissolution of the CDDP-containing gel in dilute hydrochloric acid. The results are shown in TABLE VII. The cisplatin stability was surprisingly and unexpectedly significantly improved in formulations with collagen which had been oxidized and acidified (i.e., formulated at a lower pH). After 21 days at 5° C., CDDP content in the non-oxidized, pH 7 collagen formulation dropped to 25% of its initial content. In contrast, after 21 days, the CDDP content of the oxidized, pH 3.7 collagen formulation was 90% of its initial content.

TABLE VII

Stability of CDDP in CDDP Gels Formulated with Oxidixed or Non-Oxidized Collagen Gels at pH 3.7 or pH 7.0

| | CDDP Content (% of initial) | | | |
|---|---|---|---|---|
| Time (days) | Non-Oxidized Collagen | | Oxidized Collagen | |
| at 5° C. | pH 7.0 | pH 3.7 | pH 7.0 | pH 3.7 |
| 0 | 100 | 100 | 100 | 100 |
| 0.17 | 93.6 | 93.3 | 101.2 | 98.7 |
| 0.29 | 89.3 | 90.3 | 100.2 | 100.0 |
| 1 | 77.8 | 80.7 | 95.9 | 99.8 |
| 2 | 45.8 | 70.9 | 95.8 | 99.8 |
| 4 | 39.9 | 61.0 | 90.0 | 97.2 |
| 7 | 36.4 | 31.2 | 88.2 | 96.3 |
| 14 | 24.9 | 35.2 | 82.5 | 94.0 |
| 21 | 25.0 | 31.2 | 75.5 | 92.2 |

What is claimed is:

1. Oxidized collagen wherein the thiomethyl group of one or more of the methionine residues of the collagen have been replaced by methylsulfoxy and/or methylsulfonyl groups.

2. A pharmaceutical composition comprising:
   (a) oxidized collagen wherein the thiomethyl group of one or more of the methionine residues of the collagen have been replaced by methylsulfoxy and/or methylsulfonyl groups; and
   (b) a pharmaceutical drug.

3. The pharmaceutical composition of claim 2, wherein at least 20% of the thiomethyl groups have been replaced by methylsulfoxy and/or methylsulfonyl groups.

4. The pharmaceutical composition of claim 3, wherein at least 40% of the thiomethyl groups have been replaced by methylsulfoxy and/or methylsulfonyl groups.

5. The pharmaceutical composition of claim 4, wherein at least 60% of the thiomethyl groups have been replaced by methylsulfoxy and/or methylsulfonyl groups.

6. The pharmaceutical composition of claim 2, wherein the pharmaceutical drug is compatible with non-oxidized collagen.

7. The pharmaceutical composition of claim 2, wherein the pharmaceutical drug is non-compatible with non-oxidized collagen.

8. A pharmaceutical composition comprising:
   (a) oxidized collagen wherein the thiomethyl group of one or more of the methionine residues of the collagen have been replaced by methylsulfoxy and/or methylsulfonyl groups or a mixture thereof; and
   (b) a pharmaceutical drug
wherein the pH of the pharmaceutical composition is less than about 4.5.

9. The pharmaceutical composition of claim 8, wherein the pH of the collagen is from about 2.5 to 4.5.

10. The pharmaceutical composition of claim 2 or 8, wherein the concentration of collagen in the composition is about 3% w/w or lower.

11. The pharmaceutical composition of claim 10, wherein the concentration of the collagen in the composition is from about 1% w/w to about 3% w/w.

* * * * *